United States Patent
Popovic et al.

(10) Patent No.: US 10,414,792 B2
(45) Date of Patent: Sep. 17, 2019

(54) ROBOTIC GUIDANCE OF ULTRASOUND PROBE IN ENDOSCOPIC SURGERY

(71) Applicant: KONINKLIJKE PHILIPS N.V., Eindhoven (NL)

(72) Inventors: Aleksandra Popovic, New York, NY (US); Haytham Elhawary, New York, NY (US); Christopher Stephen Hall, Kirkland, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1164 days.

(21) Appl. No.: 14/361,943

(22) PCT Filed: Nov. 27, 2012

(86) PCT No.: PCT/IB2012/056758
§ 371 (c)(1),
(2) Date: May 30, 2014

(87) PCT Pub. No.: WO2013/080124
PCT Pub. Date: Jun. 6, 2013

(65) Prior Publication Data
US 2014/0343571 A1    Nov. 20, 2014

Related U.S. Application Data

(60) Provisional application No. 61/556,625, filed on Nov. 7, 2011.

(51) Int. Cl.
*A61B 34/30*  (2016.01)
*A61B 90/00*  (2016.01)
(Continued)

(52) U.S. Cl.
CPC ........... *C07J 43/003* (2013.01); *A61B 1/0005* (2013.01); *A61B 8/12* (2013.01); *A61B 8/4218* (2013.01);
(Continued)

(58) Field of Classification Search
CPC .............................. A61B 34/30; A61B 90/361
See application file for complete search history.

(56) References Cited

U.S. PATENT DOCUMENTS 6,032,673 A    3/2000  Savage et al.
8,287,522 B2  10/2012  Moses et al.
(Continued)

FOREIGN PATENT DOCUMENTS

JP    2001275931 A    10/2001

OTHER PUBLICATIONS

Chae, P., et al., "Tandem facial amphiphiles for membrane protein stabilization," JAGS Communications (2010) 132(47): 16750-16752.
(Continued)

*Primary Examiner* — Tse W Chen
*Assistant Examiner* — Jason M Ip (57) ABSTRACT

Systems and methods for surgical robotic guidance include a robotic system (124) having a robot (122) configured to pass to a target through a port (134). The robotic system includes a visual component (102) employed in guiding the robot along a path to a location. The location is defined in accordance with a position and orientation of the robot. An ultrasonic probe (125) is guided by the robot to the location to permit engagement of the probe to collect ultrasonic images at the location.

9 Claims, 7 Drawing Sheets

(51) Int. Cl.
  A61B 1/00    (2006.01)
  A61B 8/12    (2006.01)
  A61B 8/00    (2006.01)
  C07J 43/00   (2006.01)
  A61K 47/26   (2006.01)
  A61K 47/28   (2006.01)
  C07J 9/00    (2006.01)
  C07J 31/00   (2006.01)
  C07J 41/00   (2006.01)
  C07J 51/00   (2006.01)
  C07K 1/14    (2006.01)
  A61K 9/107   (2006.01)

(52) U.S. Cl.
  CPC ............ *A61B 34/30* (2016.02); *A61B 90/361* (2016.02); *A61K 47/26* (2013.01); *A61K 47/28* (2013.01); *C07J 9/00* (2013.01); *C07J 31/006* (2013.01); *C07J 41/0061* (2013.01); *C07J 51/00* (2013.01); *C07K 1/145* (2013.01); *A61B 2034/301* (2016.02); *A61B 2090/3782* (2016.02); *A61B 2090/3784* (2016.02); *A61K 9/107* (2013.01)

(56) References Cited

U.S. PATENT DOCUMENTS

| | | | |
|---|---|---|---|
| 8,965,583 B2 | 2/2015 | Ortmaier et al. | |
| 8,998,797 B2 | 4/2015 | Omori | |
| 2004/0010190 A1 | 1/2004 | Shahidi | |
| 2004/0034297 A1 | 2/2004 | Darrow et al. | |
| 2007/0021738 A1 | 1/2007 | Hasser et al. | |
| 2007/0238981 A1 | 10/2007 | Zhu et al. | |
| 2008/0051655 A1 | 2/2008 | Masatoshi et al. | |
| 2009/0036902 A1* | 2/2009 | DiMaio | A61B 8/12 606/130 |
| 2009/0192519 A1 | 7/2009 | Omori | |
| 2009/0247875 A1* | 10/2009 | Kuniyasu | A61B 8/12 600/459 |
| 2011/0130659 A1 | 6/2011 | Cinquin et al. | |
| 2015/0011739 A1 | 1/2015 | Chae et al. | |

OTHER PUBLICATIONS

Chae, P., et al., "Maltose-neopentyl glycol (MNG) amphiphiles for solubilization, stabilization and crystallization of membrane proteins," Nature America, Inc. (2010) 7(12): 1003-1008.

Cheng, Y., et al., "Facial Amphiphiles," J. Am. Chem Soc. (1992) 114 (18): 7319-7320.

Hjelmeland, L., "The design and synthesis of detergents for membrane biochemistry", Methods in Enzymology (1986) 124: 135-164.

Hovers, J., et al., "A class of mild surfactants that keep integral membrane proteins water-soluble for functional studies and crystallization", Molecular Membrane Biology (2011) 28 (3): 171-181.

McGregor, C.L., "Lipopeptide detergents designed for the structural study of membrane proteins," Nature Publishing Group (2003) 21: 171-176.

Rosenbaum, D.M. et al., "Structure and function of an irreversible agonist-beta2 adrenoceptor complex," Nature (2011) 469: 236-240.

Rasmussen, S.G.F., et al., "Structure of a nanobody-stabilized active state of the beta2 adrenoceptor," Nature (2011) 469: 175-180.

Schafmeister, C., et al., "Structure at 2.5 A of a Designed peptide that maintains solubility of membrane proteins," Science (1993) 262: 734-738.

Zhang, Q., et al., "Designing facial amphiphiles for the stabilization of integral membrane proteins", Wiley-VCH Verlag GmbH & Co. (2007) 46: 7023-7025.

* cited by examiner

ROBOTIC GUIDANCE OF ULTRASOUND PROBE IN ENDOSCOPIC SURGERY

CROSS-REFERENCE TO PRIOR APPLICATIONS

This application is the U.S. National Phase application under 35 U.S.C. § 371 of International Application Serial No. PCT/IB2012/056758, filed on Nov. 27, 2012, which claims the benefit of U.S. Application Ser. No. 61/556,625, filed on Dec. 3, 2011. These applications are hereby incorporated by reference herein.

This disclosure relates to robotic guidance and more particularly to robotically guided ultrasonic probes for surgical imaging.

Coronary bypass surgery is a procedure in which a diseased coronary artery is abridged using an artery grafted elsewhere in the body. In minimally invasive bypass surgery, access to arteries is limited by the following factors: 1) Arteries are covered with fatty tissue or may run intramyocardially which makes them invisible in endoscope images; and 2) Due to limited motion permitted through ports, it is difficult to manually reach specific areas of the heart. These factors pose limitations for use of intraoperative US in minimally invasive bypass surgery.

In accordance with the present principles, systems and methods for surgical robotic guidance include a robotic system having a robot configured to pass to a target through a port. The robotic system includes a visual component employed in guiding the robot along a path to a location. The location is defined in accordance with a position and orientation of the robot. An ultrasonic probe is guided by the robot to the location to permit engagement of the probe to collect ultrasonic images at the location.

Another system for surgical robotic guidance includes a robotic system having a robot configured to pass to a target through a port to a location. The robotic system includes an ultrasonic probe guided by the robot to the location to permit engagement of the probe to collect ultrasonic images at the location. A passive arm is coupled to a visual component and employed in separately guiding the visual component to the location. The location is defined in accordance with a position and orientation of the robot.

A method for surgical robotic guidance includes introducing a robot having a visual guidance component to pass through a port to a target; defining a path to a location of the target for the robot; and in accordance with a position and orientation of the robot, guiding an ultrasonic probe along the path to permit engagement of the probe to collect ultrasonic images at positions along the path.

Another method for surgical robotic guidance includes introducing a robot configured to pass to a target through a first port; guiding an ultrasonic probe by the robot to a location to permit engagement of the probe to collect ultrasonic images at the location; and separately guiding a visual component to the location through a second port, the location being defined in accordance with a position and orientation of the robot.

This disclosure will present in detail the following description of preferred embodiments with reference to the following figures wherein.

In accordance with the present principles, a system, apparatus and method are provided that enable ultrasound (US) scanning of endoluminal vessels and in particular coronary arteries in minimally invasive procedures and in particular, bypass surgery, using a robotically steered ultrasound probe. In this way, immediate evaluation of success of revascularization in coronary artery bypass surgery is performed with the ultrasound probe. In minimally invasive surgery, this operation is very complex given difficult handling of instruments through ports. Also, arteries may not be visible if they are intramyocardial or covered with fibrous-fatty tissue. Approximately 500,000 coronary bypass procedures are performed per year in the United States alone. Most of those procedures are done on more than one vessel. The present principles provide for ultrasound scanning, which is complementary to endoscopically assisted robot technology. The robot provides a repeatable instrument mounting position which is immune from port limitations and other conditions.

In one embodiment, a robotic endoscope assistant is configured to permit replacement of an endoscope with a US probe. In another embodiment, the robot with an US probe uses cameras in one or more of ports, instruments or the actual US probe to provide visual feedback.

In yet another embodiment, the endoscope and the US probe are placed in one mechanical fixture that permits actuation of the US probe along the fixture. In endoscope mode, the US is retracted and inactive. Once a user selects an area or an artery to investigate, the US probe slides out of a fixture to achieve acoustic coupling and collect image data. In still another embodiment, the ultrasound is introduced through an instrument port with the endoscope intact, and the robot is decoupled from the endoscope and attached to the US probe. In all of these illustrative embodiments, the user can either select a manual path for the US probe or can select a path (e.g., an artery) from an overlay in endoscope images.

It should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, heart, gastro-intestinal tract, excretory organs, brain, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), DVD and Blu-ray™.

Figure 1:
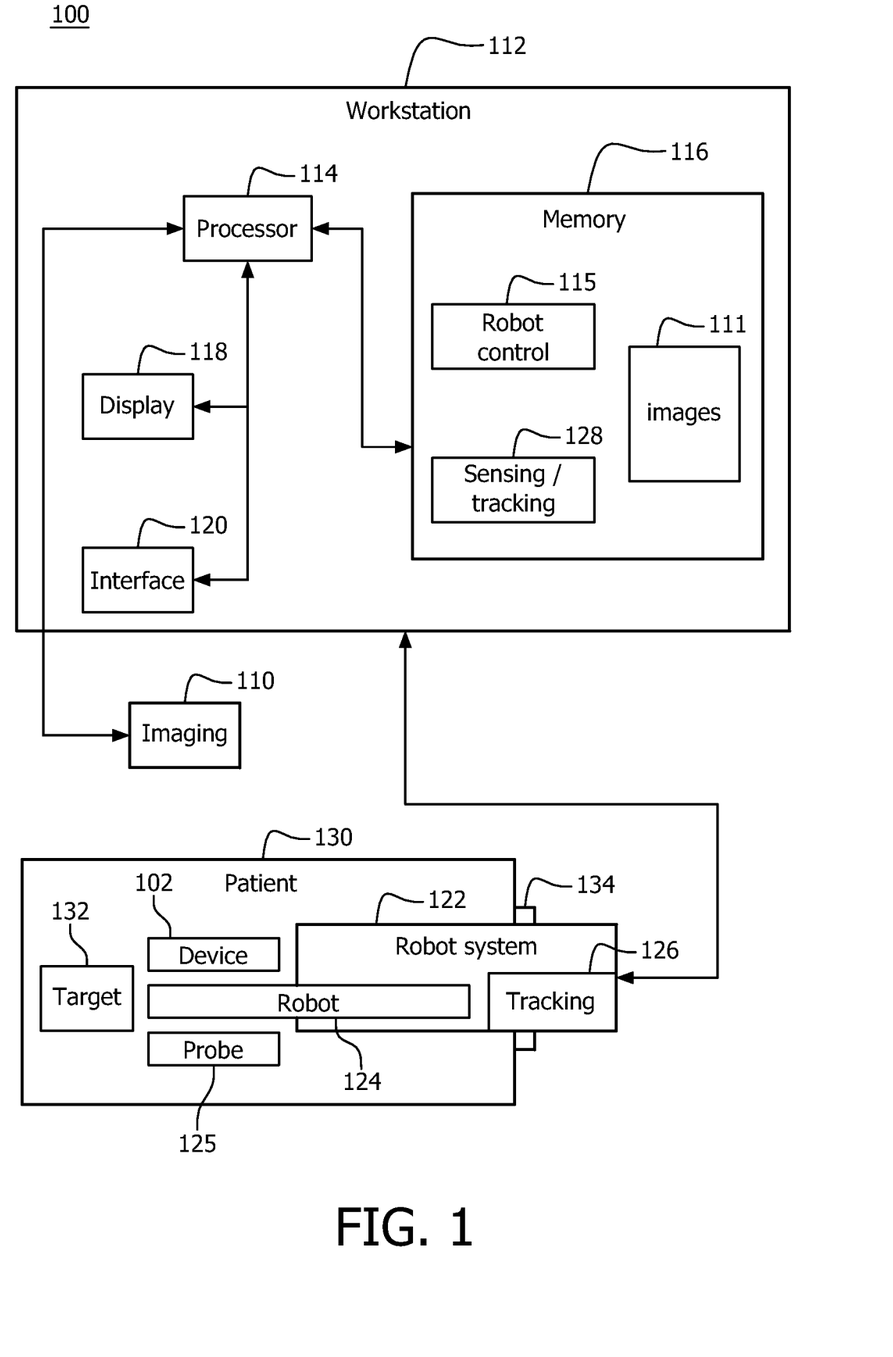
FIG. 1 is a block/flow diagram showing a system for surgical robotic guidance in accordance with one illustrative embodiment.

Referring now to the drawings in which like numerals represent the same or similar elements and initially to FIG. 1, a system 100 for performing a medical procedure is illustratively depicted. System 100 may include a workstation or console 112 from which a procedure is supervised and managed. Workstation 112 preferably includes one or more processors 114 and memory 116 for storing programs and applications. Memory 116 may store a robot control module 115 configured to control servos, actuators or the like for a repeatably controlling positions or orientations of a mechanism or robot system 122. The robot system 122 may include a sensing/tracking device or devices 126 to provide feedback signals to ensure positional accuracy, a robot or linkage 124 and other devices or sensors for proper operation of the robot 124. Such devices 126 may include fiber optic sensors, encoders, electromagnetic tracking, or the like. A sensing/tracking module 128 may be provided to interpret feedback from the device or devices 126. In one embodiment, sensing/tracking module 128 is configured to use signal feedback from sensing devices 126 or the robot system 122 to reconstruct deformations, deflections and other changes associated with the robot 124.

Workstation 112 may include a display 118 for viewing internal images of a subject if an imaging system 110 is employed. The imaging system 110 may include, e.g., a magnetic resonance imaging (MRI) system, a fluoroscopy system, a computed tomography (CT) system, ultrasound (US), etc. Display 118 may also permit a user to interact with the workstation 112 and its components and functions. This is further facilitated by an interface 120 which may include a keyboard, mouse, a joystick or any other peripheral or control to permit user interaction with the workstation 112.

Imaging system 110 may be provided for collecting pre-operative imaging data or real-time intra-operative imaging data. The pre-operative imaging may be performed at another facility, location, etc. in advance of any procedure. Images 111 may be stored in memory 116, and may include pre-operative 3D image volumes of a patient or pathway system.

A medical device 102 is preferably elongated and may include, e.g., a catheter, a guide wire, an endoscope, a probe, a robot, an electrode, a filter device, a balloon device, or other medical component, etc. In one embodiment, an endoscope is employed for the medical device 102 and is guided to a position within a patient using the robot 124. When a desired position is reached, feedback from the robot 124 may be stored to ensure that the position can be re-obtained in subsequent activities. In one embodiment, an endoscope (102) is employed to find a location; then the endoscope (102) is removed and an ultrasonic (US) probe 125 is positioned by the robot 124 at the same location. The US probe 125 can now be positioned in contact with tissue to image a region corresponding to the endoscopically determined location. Since the robot 124 is employed, the location is repeatably obtained by the US probe 125. Methods for overlaying an arterial tree on endoscope images may be employed to provide visibility of arteries in images. These overlays may be employed for robotic navigation to ensure reproducible point location. The robot 124 may follow the arterial path in endoscope images. Other robotic navigation techniques may also be employed.

In many embodiments, the device 102 and probe 125 are introduced in a patient 130 through ports 134, e.g., ports to a thoracic cavity, etc. Intraoperative ultrasound (US) may be used in coronary bypass surgery to assess the function of blood vessels. US may be used before bypass is completed to detect positions of arterial plaque or after the bypass is placed to assess blood flow through the bypass, aorta, or other coronary arteries. The ultrasound probe 125 is placed on or in a sterile sheath and moved on a heart surface to collect US images. Minimally invasive bypass surgery is performed through small ports 134 (e.g., between 5 mm for totally endoscopic procedures and 50-60 mm for minimally invasive direct bypass surgery). The present principles include robotic steering of a US probe 125 to systematically scan arteries and other areas of interest. The robot 124 holds the imaging probe 125 for deployment in accordance with the endoscopic images or planned pathway. The robot 124 can be any kind of actuated device capable of moving around a fulcrum point at a chest surface (e.g., through port(s) 134) or other entry point on the patient 130. The robot 124 conveys one or more of the US probe 125 and a visual component (e.g., camera, endoscope, etc.) to a target 132. In this way, the target can be analyzed visually and ultrasonically from a same repeatably obtained location. The robot 124 provides highly accurate coordinates from which US imaging and visual imaging may be obtained from a same otherwise obscured location.

Figure 2:
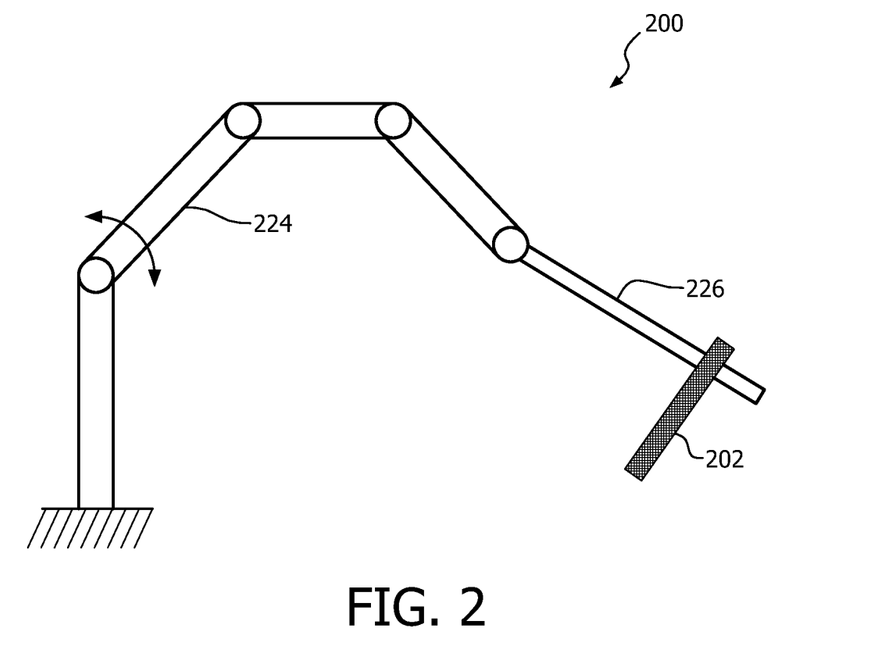
FIG. 2 is a schematic diagram showing a robotic system where a robot carries a visual component and an ultrasonic probe at separate times in accordance with one illustrative embodiment.

Referring to FIG. 2, an illustrative robotic system 200 with an imaging device 202 is shown in accordance with one embodiment. In this embodiment, a robot 224 steers an endoscope (202). Additional functionality is provided through replacement of the endoscope with an ultrasound probe (202). The imaging device 202 is shown generically and is detachable from the robot 224 (which may be the same as robot 124 in FIG. 1). The device 202 may be a detachable endoscope or a detachable US transducer. With the endoscope placed through a port, a surgeon or user chooses a path on an endoscope image as shown, e.g., in FIG. 3.

Figure 3:
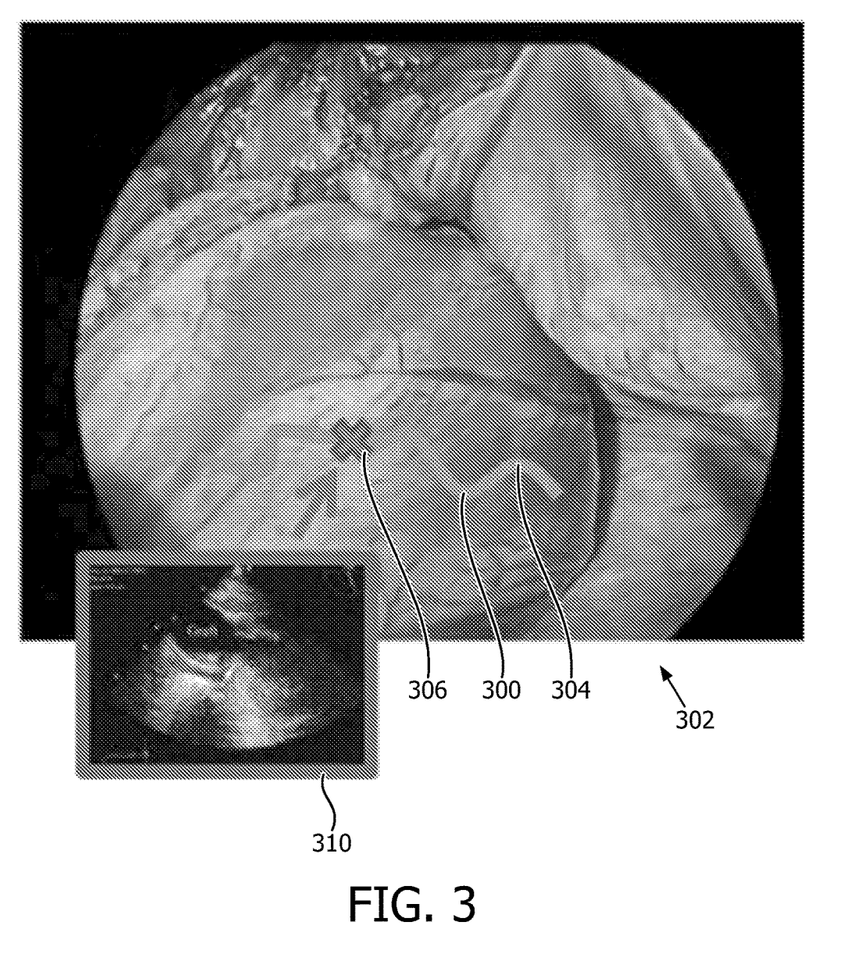
FIG. 3 is an image showing a mapped path along a blood vessel and an illustrative ultrasonic image taken at a point on the path in accordance with one illustrative embodiment.

Referring to FIG. 3, a path 300 is identified in an endoscopic image 302 and an overlay 304 is positioned over the path. A user interface 120 may be employed for the selection of the path. The surgeon chooses the path which can be a manually selected curve, an artery/vein, etc. For example, the path 300 may include a blood vessel selected in the pre-operative images, etc.

The endoscope is replaced with the US probe and the path is followed with US probe collecting a series of images. Every image is associated with a point on the path. After the operation is completed, the user can slide a virtual point 306 on the path to select different US images. An inset 310 shows an US image taken at virtual point 306.

The path 300 can be defined by manual input, for example, with a computer mouse, or can be selected as an artery from the pre-operative arterial overlay. Additionally, the path 300 can be selected on the pre-operative images (111, FIG. 1) (for example selecting an artery or a series of landmarks), and transferred to the current endoscope image and used to robotically control the endoscope. The path 300 could be selected on pre-operative images (111, FIG. 1) and then mapped to the endoscope image 302.

Referring again to FIG. 2, after the path 300 is selected, the endoscope is replaced with the ultrasound probe. The robot 224 moves the probe 202 towards a target to secure acoustic coupling. This can be done by the surgeon using some input device (such as a mouse, joystick or controls on a user interface 120, FIG. 1) or automatically using force control or other methods related to the US image.

One example employs a method of knowing depth which has the US probe located in a pre-defined specific manner with respect to an end effector 226 of the robot 224, thus defining the relationship between the end effector 226 and US probe images, allowing depth of structures from the robot 224 to be obtained from the US image. Once the US probe is positioned correctly close to the heart or other target, the robot 224 moves the probe along the predefined path. As the US probe (202) is moving, a position of the probe (202) relative to the path is known. After all images are collected, the user can replay the path (300) by using a sliding function on the path or selecting a specific point (e.g., using the workstation 112 with display 118 and interface 120). In addition, the robot 224 can move the probe (202) in different directions to obtain images in different planes relative to the anatomy. This will permit imaging of both cross sections, coronal and sagittal images of the targeted structure, etc.

Figure 4:
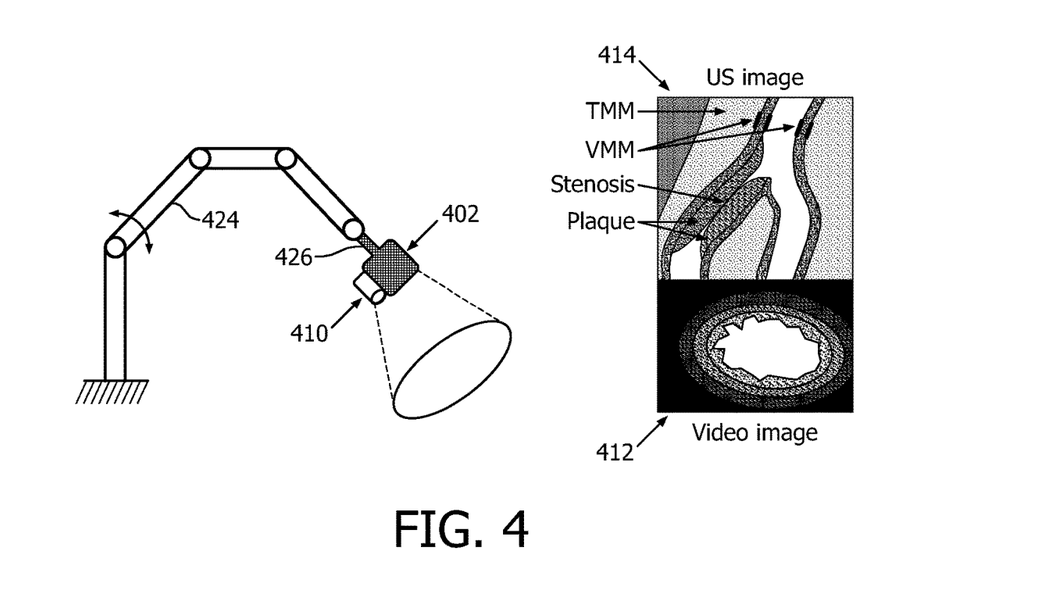
FIG. 4 is a schematic diagram showing a robotic system where a robot carries a camera and an ultrasonic probe concurrently in accordance with one illustrative embodiment.

Referring to FIG. 4, in another embodiment, a US probe 402 is connected to an end effector 426 of a robot 424. In addition, a camera or cameras 410 are added. Visual feedback of the US probe 402 and a surgical region may be provided while the robot 402 is moving. The cameras 410 can be added by, for example, attaching a small camera 410 to the US probe 402, which would provide visual feedback coupled with the US images of the targeted structure. The robot 424 holds the US probe 402 and moves along a predefined path providing visual feedback of the probe 402 using camera 410, which may be attached to the probe 402. Both visual 412 and ultrasonic 414 images can be combined or individually shown to the surgeon or user.

Figure 5:
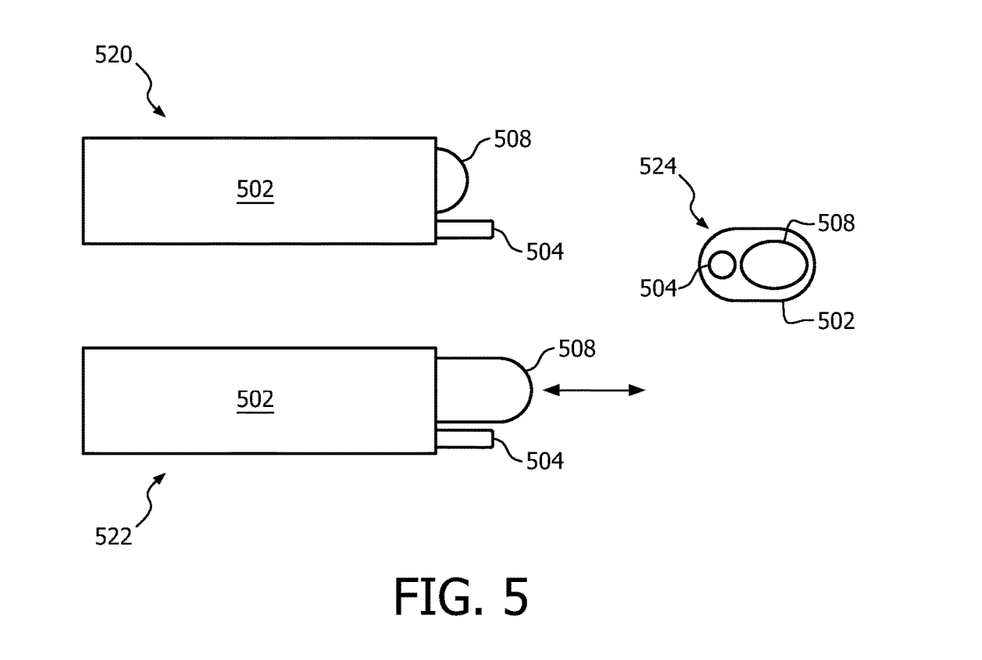
FIG. 5 is a schematic diagram showing a housing or fixture for a robotic system that carries an endoscope and an ultrasonic probe concurrently where the ultrasonic probe is extendable or adjustable into an operative position in accordance with one illustrative embodiment.

Referring to FIG. 5, three views of a housing or fixture 502 are depicted. A first view 520 shows an endoscopic mode where an endoscope 504 is employed. A second view 522 shows an ultrasonic mode where an ultrasonic probe 508 is extended to gather US images. A third view 524 shows a front view of the housing 502. In this embodiment, the endoscope 504 and the ultrasound probe 508 are packaged in a single fixture 502. In the embodiment depicted, the probe 508 is permitted to slide along a longitudinal axis of the fixture 502. The US probe 508 and endoscope 504 are placed in the fixture or housing 502 with US probe 508 able to move relative to the housing 502 to be able to make contact with tissue to acquire images.

In an endoscope mode (view 520), the US probe 508 is retracted and inactive. As the path is selected, the US probe 508 is moved outward (view 522) until tissue coupling is achieved. The US probe 508 is activated, and the collection of images is performed, as described above. One advantage is that visual feedback is provided by the endoscope 504 during US image collection. This embodiment may need a larger port to accommodate the larger housing or fixture 502. It may be possible to introduce very small US probes together with an endoscope without using larger sized ports.

Figure 6:
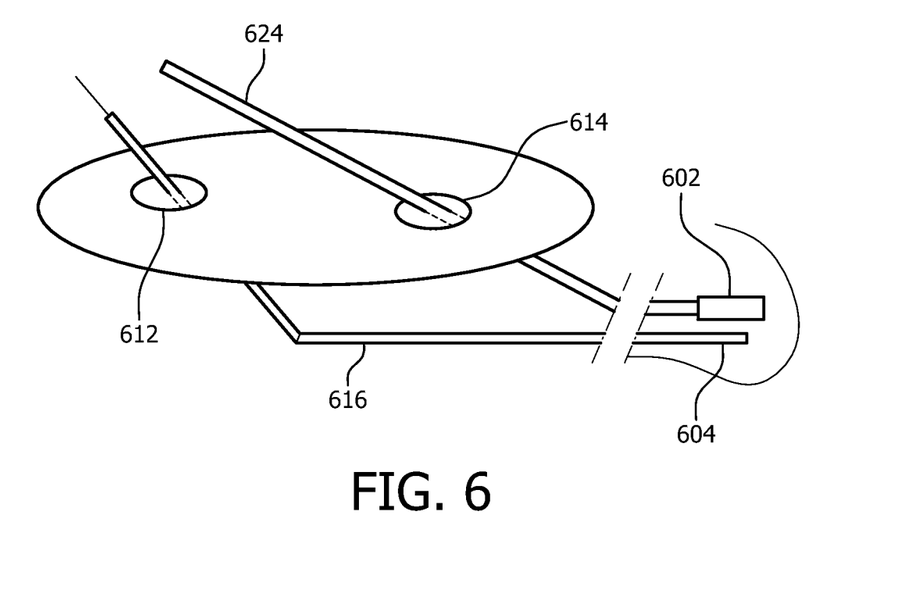
FIG. 6 is a schematic diagram showing a robotic system where a robot carries an ultrasonic probe and a passive arm that separately carries a visual component, the robot and the passive arm being deployed from separate ports in accordance with one illustrative embodiment.

Referring to FIG. 6, another embodiment employs two small instrument ports 612 and 614. In this embodiment, an endoscope 604 is fixed using a passive holding arm 616 or is held by a human through instrument port 612. The passive holding arm 616 may include any number of devices, such as a catheter, push rod, wire, etc. A robot 624 is equipped with an ultrasound probe 602 and introduced through the instrument port 614. The endoscope 604 and probe 602 are independently provided. The endoscope 604 is employed to visually locate the robot 624 and probe 602. This permits the use of small ports and visual feedback. In addition, a position of the robot 624 is known and can be employed to pinpoint a point of view for the US images.

While the present principles are applicable to any interventional procedure, a particularly useful application includes coronary bypass surgery. The present embodiments can be employed in other endoscopic vascular surgeries or where US imaging of structures during minimally invasive surgery is convenient and useful.

Figure 7:
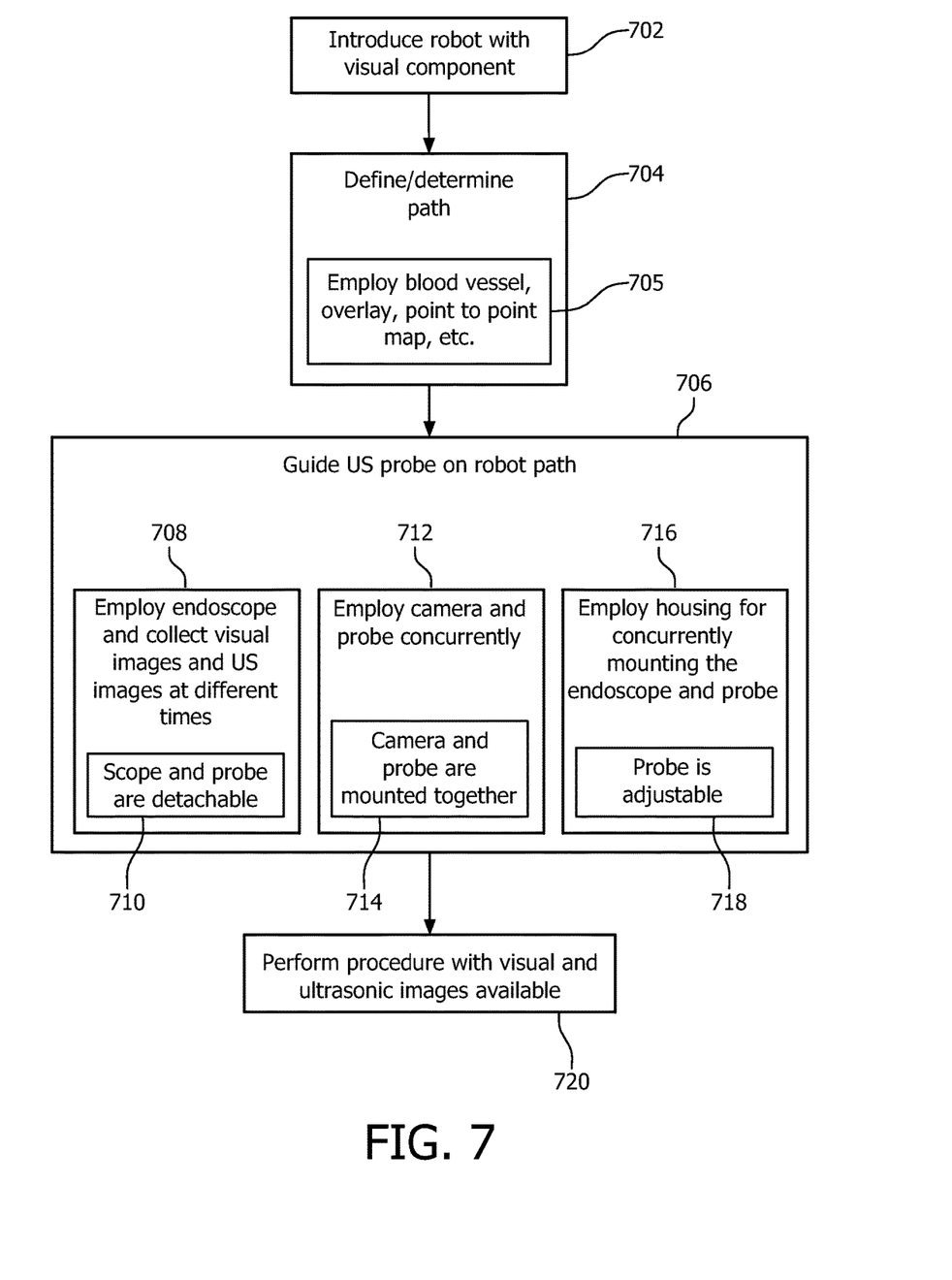
FIG. 7 is a flow diagram showing methods for surgical robotic guidance for collecting ultrasonic images in accordance with illustrative embodiments.

Referring to FIG. 7, methods employing surgical robotic guidance for collecting ultrasonic images are illustratively shown. In block 702, a robot is introduced having a visual guidance component to pass to a target preferably through surgical ports. In block 704, a path or target marker is defined at a location on the target for the robot. The robot may be guided along the path by using previously obtained images or by using guideposts collected during the deployment of the robot. In addition, known tracking techniques may be employed to locate or guide the robot to the target. In block 705, the path may be determined based on one or more of the following techniques. A blood vessel may be followed or traced to provide the path, a point to point mapping in an image may be employed and then provided to the robot system for control commands, and an overlay may be placed on an image and followed, etc.

In block 706, in accordance with a position and orientation of the robot, an ultrasonic probe is guided along the path to permit engagement of the probe to collect ultrasonic images at positions along the path. The ultrasonic probe may be deployed contemporaneously with the visual component or may be deployed at a different time. In block 708, the visual component may include an endoscope, and the endoscope is deployed first and then the ultrasonic probe is deployed such that visual images and ultrasonic images are taken at different times. In block 710, the endoscope and the probe are detachable from the robot and are employed separately in a same procedure. In block 712, the visual component includes a camera, and the camera and the ultrasonic probe are deployed concurrently. In block 714, the camera may be mounted on the ultrasonic probe, and visual images and ultrasonic image are acquired concurrently from a same vantage point. In block 716, a housing or fixture is coupled to an end effector of the robot and configured to deploy an endoscope—as the visual component—and the ultrasonic probe, concurrently, wherein the ultrasonic probe may be actuated or deployed from within the housing to engage tissue for acquiring images. In block 718, the ultrasonic probe moves along a longitudinal axis of the housing. Other movements or positioning systems may also be employed.

In block 720, a procedure is carried out where the location is accurately known due to the robot, and US images may be collected at the accurately known location. This may include providing US images along a defined path. Advantageously, visual and US imaging are provided together. In a cardiac bypass surgery example, this enables viewing of a bypass for bleeding (visual) while checking flow characteristics (US) through the bypass. Other advantages and applications are also contemplated.

Figure 8:
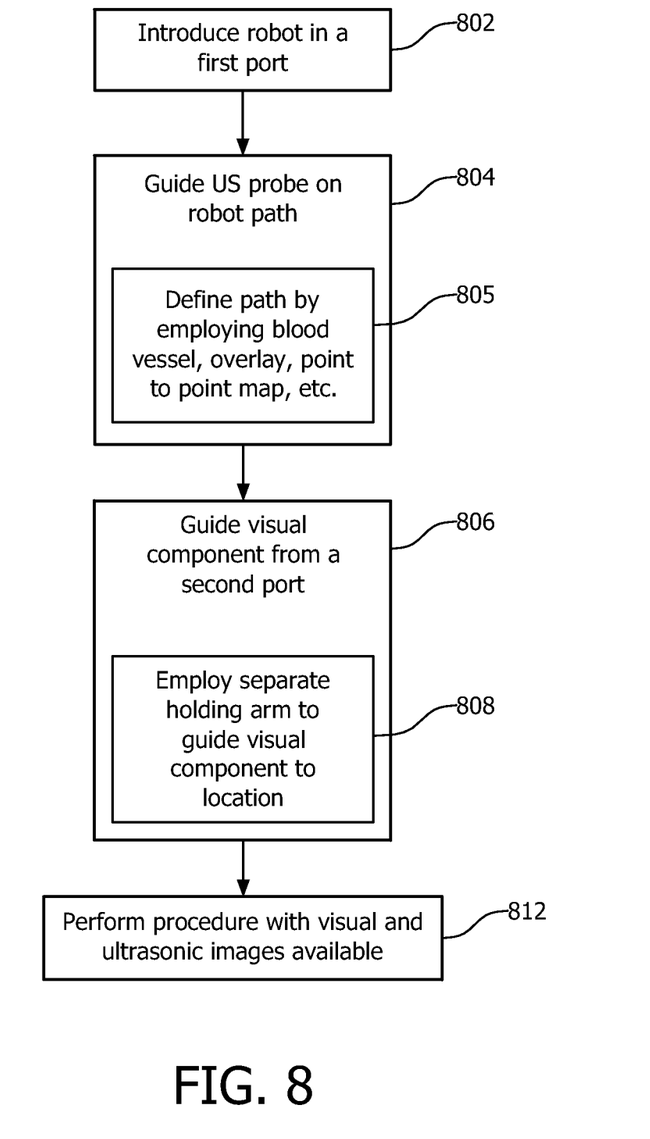
FIG. 8 is a flow diagram showing a method for surgical robotic guidance for collecting ultrasonic images in accordance with another illustrative embodiment.

Referring to FIG. 8, another method for surgical robotic guidance for collecting ultrasonic images is illustratively shown. In block 802, a robot is introduced, which is configured to pass to a target location through a first port. In block 804, an ultrasonic probe is guided by the robot to the location to permit engagement of the probe to collect ultrasonic images at the location. In block 805, the path may be determined based on one or more of the following techniques. A blood vessel may be followed or traced to provide the path, a point to point mapping in an image may be employed and then provided to the robot system for control commands, and an overlay may be placed on an image and followed, etc.

In block 806, a visual component is separately guided to the location through a second port. The location is defined in accordance with a position and orientation of the robot. Data from the robot may be employed to provide guidance to the location for the visual component. The guidance would be visual as the robot can be visually followed to the location. The visual component may include, e.g., an endoscope or a camera. In block 808, separate guidance of the visual components may be employed with a passive holding arm to guide the visual component to the location.

In block 812, a procedure is carried out where the location is accurately known due to the robot, and US images may be collected at the accurately known location. This may include providing US images along a defined path. In a cardiac bypass surgery example, this enables viewing of a bypass for bleeding (visual) while checking flow characteristics (US) through the bypass. Other advantages and applications are also contemplated.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for robotic guidance of an ultrasound probe in endoscopic surgery (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for surgical robotic guidance, comprising:
   a robotic system having a robot configured to pass to a target through a port, the robotic system including a visual component employed in guiding the robot along a path to a location, the location being defined in accordance with a position and orientation of the robot; and
   an ultrasonic probe guided by the robot to the location to permit engagement of the probe to collect ultrasonic images at the location,
   wherein the visual component includes an endoscope and the robot deploys the endoscope first and then deploys the ultrasonic probe such that visual images and ultrasonic images are taken at different times but at the same location.

2. The system as recited in claim 1, wherein the endoscope and the probe are detachable from the robot and are employed sequentially.

3. The system as recited in claim 1, wherein the path is determined based on one or more of: a pre-operative image, a blood vessel image, a point to point mapping in an image and an overlay on an image.

4. A method for surgical robotic guidance, comprising:
   introducing a robot having a visual guidance component to pass to a target through a port; defining a path to a location of the target for the robot; and
   in accordance with a position and orientation of the robot, guiding an ultrasonic probe along the path to permit engagement of the probe to collect ultrasonic images at positions along the path,
   wherein the visual component includes an endoscope and the method further comprises deploying the endoscope first and then deploying the ultrasonic probe such that visual images and ultrasonic images are taken at different times.

5. The method as recited in claim 4, wherein the endoscope and the probe are detachable from the robot and are employed separately in a same procedure.

6. The method as recited in claim 4, wherein the path is determined based on one or more of: a pre-operative image, a blood vessel image, a point to point mapping in an image and an overlay on an image.

7. A method for surgical robotic guidance, comprising:
introducing a robot configured to pass to a target through a first port; guiding an ultrasonic probe by the robot to a location to permit engagement of the probe to collect ultrasonic images at the location; and
separately guiding a visual component to the location through a second port, the location being defined in accordance with a position and orientation of the robot,
wherein the visual component includes one of an endoscope and a camera.

8. The method as recited in claim 7, wherein separately guiding includes employing a passive arm to guide the visual component.

9. The method as recited in claim 7, wherein the path is determined based on one or more of: a pre-operative image, a blood vessel image, a point to point mapping in an image and an overlay on an image.

* * * * *